(12) United States Patent
Gao et al.

(10) Patent No.: US 10,531,401 B2
(45) Date of Patent: Jan. 7, 2020

(54) METHOD, TERMINAL DEVICE AND SYSTEM FOR CONTROLLING TRANSMISSION

(71) Applicant: Xiaomi Inc., Beijing (CN)

(72) Inventors: Yuan Gao, Beijing (CN); Xiaohui Pi, Beijing (CN); Xiaogang Jiao, Beijing (CN)

(73) Assignee: XIAOMI INC., Beijing (CN)

( * ) Notice: Subject to any disclaimer, the term of this patent is extended or adjusted under 35 U.S.C. 154(b) by 144 days.

(21) Appl. No.: 14/512,375

(22) Filed: Oct. 10, 2014

(65) Prior Publication Data

US 2015/0271766 A1 Sep. 24, 2015

Related U.S. Application Data

(63) Continuation of application No. PCT/CN2014/082923, filed on Jul. 24, 2014.

(30) Foreign Application Priority Data

Mar. 20, 2014 (CN) .......................... 2014 1 0106272

(51) Int. Cl.
*H04W 52/28* (2009.01)
*A61B 5/00* (2006.01)
*H04B 1/3827* (2015.01)

(52) U.S. Cl.
CPC ......... *H04W 52/281* (2013.01); *A61B 5/6801* (2013.01); *H04B 1/3838* (2013.01)

(58) Field of Classification Search
CPC .............. H04W 52/281; H04W 52/287; H04B 1/3838; A61B 5/681; A61B 5/0022; A61B 5/6801
See application file for complete search history.

(56) References Cited

U.S. PATENT DOCUMENTS

2007/0274531 A1\* 11/2007 Camp ...................... H04R 5/04
381/74
2009/0015413 A1\* 1/2009 Gelabert .............. A61B 5/0031
340/572.1
(Continued)

FOREIGN PATENT DOCUMENTS

CN 1231570 A 10/1999
CN 1830223 A 9/2006
(Continued)

OTHER PUBLICATIONS

"International Search Report for PCT/CN2014/082923".
(Continued)

*Primary Examiner* — Yuwen Pan
*Assistant Examiner* — Fatuma G Sherif
(74) *Attorney, Agent, or Firm* — Jun He Law Offices P.C.; James J. Zhu

(57) ABSTRACT

The present disclosure discloses a method, a terminal device and a system for controlling transmission, relating to the field of terminal technology. In the method for controlling transmission provided by the present embodiment, a user type of a current user is acquired, and when it is determined that the user type of the current user is the user type specified to reduce radiation, the terminal device reduced a default transmission power, thereby solves the problem of strong radiation generated by a terminal device in the prior art, which adopts a default transmission mechanism for optimal signal, and further achieves an effect of reducing radiation for the user types that need to reduce radiation.

12 Claims, 6 Drawing Sheets

(56) References Cited

U.S. PATENT DOCUMENTS

| | | | |
|---|---|---|---|
| 2010/0056210 A1* | 3/2010 | Bychkov | H04B 1/3838 455/556.1 |
| 2010/0159835 A1 | 6/2010 | Aoki et al. | |
| 2010/0160744 A1* | 6/2010 | Ha | H04W 4/02 600/301 |
| 2011/0309941 A1 | 12/2011 | Hyde et al. | |
| 2012/0257657 A1 | 10/2012 | Subrahmanya et al. | |
| 2012/0315847 A1* | 12/2012 | Li | H03K 17/975 455/41.1 |
| 2012/0315862 A1 | 12/2012 | Okano et al. | |
| 2013/0172039 A1 | 7/2013 | Drucker et al. | |
| 2015/0201385 A1* | 7/2015 | Mercer | H04B 1/3838 455/575.5 |

FOREIGN PATENT DOCUMENTS

| | | |
|---|---|---|
| CN | 101588401 A | 11/2009 |
| CN | 101772206 A | 7/2010 |
| CN | 101854410 A | 10/2010 |
| CN | 102184312 A | 9/2011 |
| CN | 102325365 A | 1/2012 |
| CN | 102984359 A | 3/2013 |
| CN | 103037493 A | 4/2013 |
| CN | 103460504 A | 12/2013 |
| CN | 103605504 A | 2/2014 |
| CN | 103889040 A | 6/2014 |
| EP | 1035746 A1 | 9/2000 |
| EP | 2670054 A1 | 12/2013 |
| JP | 1994140949 A | 5/1994 |
| JP | 2003179670 A | 6/2003 |
| JP | 2004512762 A | 4/2004 |
| JP | 2008306242 A | 12/2008 |
| RU | 2186585 C1 | 8/2002 |
| RU | 2611729 C1 | 7/2014 |
| WO | 2012/104476 A1 | 8/2012 |
| WO | 2012/139077 A1 | 10/2012 |

OTHER PUBLICATIONS

Partial European Search Report for 15159217.7.
Office Action from EPO for European Application 15159217.7, dated Jun. 22, 2018.
First Office Action of Application MX/a/2014/011937 of PCT national phase dated Jul. 10, 2017.

* cited by examiner

METHOD, TERMINAL DEVICE AND SYSTEM FOR CONTROLLING TRANSMISSION

CROSS-REFERENCE TO RELATED APPLICATIONS

This application is a Continuation of International Application PCT/CN2014/082923, filed on Jul. 24, 2014, which claims priority to Chinese Patent Application No. 201410106272.X, filed on Mar. 20, 2014, the entire contents of which are incorporated herein by reference.

TECHNICAL FIELD

The present disclosure generally relates to the field of terminal technology, and more particularly, to a method, a terminal device, and a system for controlling transmission.

BACKGROUND

Terminal devices such as smart phones, tablet PCs and e-book readers usually adopt electromagnetic waves to achieve wireless transfer of information, these electromagnetic waves are also be known as mobile phone radiation. But now, in order to guarantee better communication quality, a mobile phone usually emits electromagnetic waves to achieve an optimal signal. The mobile phone will use a transmission power as large as possible to guarantee the strongest signal, and consequently the mobile phone radiation will reach a maximum value as well. Although the potential harm of mobile phone radiation to humans is controversial, many specific groups of people, such as the elderly, children, patients and pregnant women should limit or avoid mobile phone usage to be safe.

During the realization of this present disclosure, it is found that the terminal devices mentioned above default to optimize their signals, which entails a large transmission strength, thereby generating strong radiation.

SUMMARY

Accordingly, the present disclosure provides a method, a terminal device and a system for controlling transmission. The technical solutions are as follows.

According to a first aspect of embodiments of the present disclosure, a method for controlling transmission in a terminal device comprises: acquiring a user type of a current user; and reducing a default transmission power if the user type of the current user is a user type specified to reduce radiation.

According to a second aspect of embodiments of the present disclosure, a method for controlling transmission in a wearable device, comprises: collecting biological parameters of a current user; determining a user type of the current user according to the collected biological parameters; and sending a type signal of the current user to a terminal device according to the user type.

According to a third aspect of embodiments of the present disclosure, a terminal device for controlling transmission comprises: a processor; and a memory for storing instructions executable by the processor, for performing: acquiring a user type of a current user; and reducing a default transmission power if the user type of the current user is a user type specified to reduce radiation.

According to a fourth aspect of embodiments of the present disclosure, a wearable device for controlling transmission comprises: a processor; and a memory for storing instructions executable by the processor, for performing: collecting biological parameters of a current user; determining a user type of the current user according to the collected biological parameters; and sending a type signal of the current user to a terminal device according to the user type.

According to a fifth aspect of embodiments of the present disclosure, a non-transitory readable storage medium comprises instructions, executable by a processor in a terminal device, for performing a method of controlling transmission, comprising: acquiring a user type of a current user; and reducing a default transmission power if the user type of the current user is a user type specified to reduce radiation.

According to a sixth aspect of embodiments of the present disclosure, non-transitory readable storage medium comprises instructions, executable by a processor in a wearable device, for performing a method of controlling transmission, comprising: collecting biological parameters of a current user; determining a user type of the current user according to the collected biological parameters; and sending a type signal of the current user to a terminal device according to the user type.

According to a seventh aspect of embodiments of the present disclosure, a system for controlling transmission comprises: a wearable device, which is configured to collect biological parameters of a current user, and send the biological parameters of the current user to a terminal device through a wired or wireless network; and a terminal device, which is configured to receive the biological parameters sent from the wearable apparatus, determine a user type of the current user according to the biological parameters, and reduce a default emission power when the user type of the current user is a user type specified to reduce radiation.

According to an eighth aspect of embodiments of the present disclosure, a system for controlling transmission comprises a wearable device, which is configured to collect the biological parameters of the current user, determine the user type of the current user according to the biological parameters, and send a type signal to the terminal device according to the user type through a wired or wireless network; and a terminal device, which is configured to receive the type signal sent from the wearable device, acquire the user type of the current user according to the type signal, and reduce a default emission power when the user type of the current user is a user type specified to reduce radiation.

According to a ninth aspect of embodiments of the present disclosure, a system for controlling transmission comprises a wearable device, which is configured to collect biological parameters of a current user; and a terminal device, which is configured to reduce a default emission power when a user type of the current user is a user type specified to reduce radiation, wherein the user type of the current user is determined based on the biological parameters of the current user.

The technical solutions provided by the embodiments of the present disclosure may include the following advantageous effects.

The user type of the current user is acquired, and when it is determined that the user type of the current user belongs to the user types specified to reduce radiation, the terminal device is controlled to reduce the default transmission power, thereby solves the problem of strong radiation generated by a terminal device in the prior art, which adopts a default transmission mechanism of optimal signal, and further achieves an effect of reducing radiation for the user types that need to reduce radiation.

It shall be understood that both the foregoing general description and the following detailed description are exemplary and explanatory only and may not limit the present disclosure.

BRIEF DESCRIPTION OF THE DRAWINGS

The accompanying drawings which are hereby incorporated in and constitute a part of this specification, illustrate embodiments consistent with the disclosure, and together with the description, serve to explain the principles of the disclosure.

DETAILED DESCRIPTION

Detailed description of the exemplary embodiments will be made herein, with examples thereof to be shown in the accompanying drawings. In the following descriptions, when the following describing refers to the accompanying drawings, unless expressed otherwise, the same number in different drawings refers to the same or similar elements. The embodiment manners described in the following exemplary embodiments do not represent all embodiments that are consistent with the present disclosure. On the contrary, they are only examples of the devices and the methods that are consistent with some of the aspects of the present disclosure as recited in the claims.

"Terminal device" mentioned herein can be any one of a mobile phone, a tablet PC, a router, an e-book reader, a MP3 (Moving Picture Experts Group Audio Layer III) player, a MP4 (Moving Picture Experts Group Audio Layer IV) player, a portable laptop computer, a desktop computer and the like.

Figure 1:
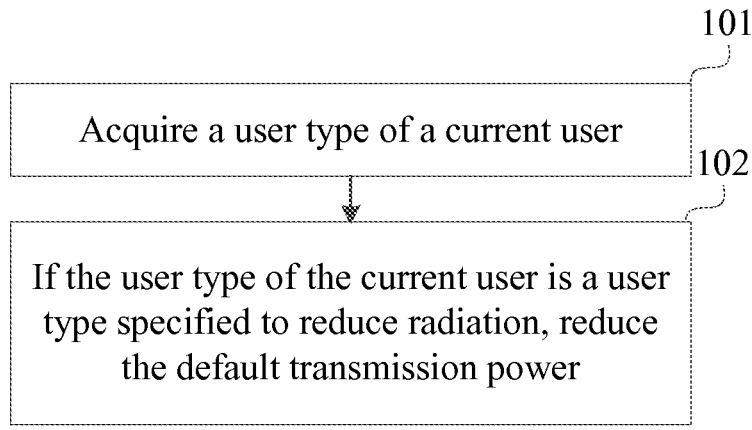
FIG. 1 is a flow diagram illustrating a method for controlling transmission, according to an exemplary embodiment of the present disclosure.

FIG. 1 is a flow diagram illustrating a method for controlling transmission, according to an exemplary embodiment. As shown in FIG. 1, the method for controlling transmission is used in a terminal device and includes the following steps.

In step S101, a user type of a current user is acquired.

The terminal device is utilized by the current user. Therefore, the user type of the current user is acquired firstly. The user type may be classified into ordinary people, elderly, children or pregnant women, wherein the elderly, the children and the pregnant women are the user types that need have radiation reduced. The user types may also be classified into healthy people, sub-healthy people or patients, wherein the sub-healthy people and the patients are the user types that need to have radiation reduced.

The user types may be acquired by a setting of a user or based on biological parameters of the user.

In step S102, when it is determined that the user type of the current user belongs to the user types specified to reduce radiation, the terminal device is controlled to reduce the default transmission power.

When a default transmission strategy is a signal priority strategy, the default transmission power usually is a transmission power, the radiation of which is the strongest.

In conclusion, in the method for controlling transmission provided by the present embodiment, the user type of the current user is acquired, and when it is determined that the user type of the current user is the user type specified to reduce radiation, the terminal device is controlled to reduce the default transmission power, thereby solves the problem of strong radiation generated by a terminal device in the prior art, which adopts a default transmission mechanism for optimal signal, and further achieves an effect of reducing radiation for the user types that need to reduce radiation.

Figure 2:
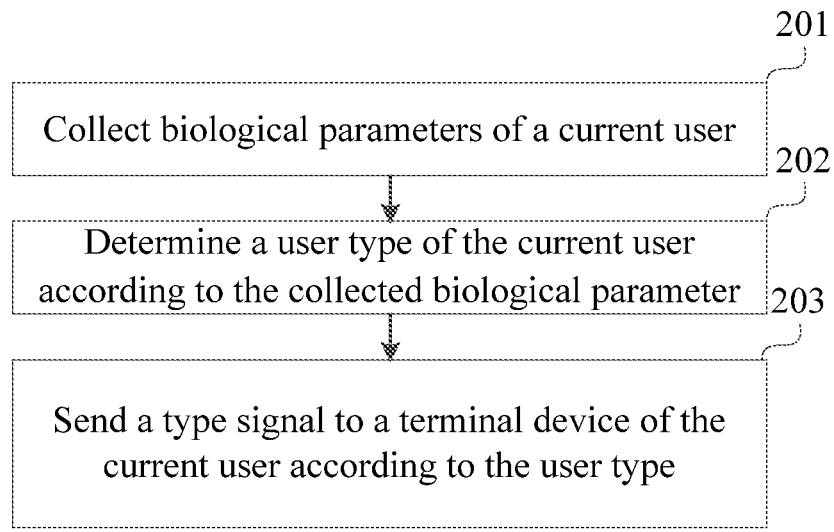
FIG. 2 is a flow diagram illustrating another method for controlling transmission, according to an exemplary embodiment of the present disclosure.

FIG. 2 is a flow diagram illustrating another method for controlling transmission, according to an exemplary embodiment. As shown in FIG. 2, the method for controlling transmission is used in a wearable device and includes the following steps.

In step S201, biological parameters of a current user are collected.

The current user wears the wearable device, which can collect biological parameters from the current user. The wearable device may be a smart bracelet or a smart watch or the like. The biological parameters include one or more parameters of heartbeat, pulse, sleep record, mood record, motion record, temperature record and calorie intake record of a user.

In step S202, a user type of the current user is determined according to the biological parameters.

In step S203, a type signal is sent to a terminal device of the current user according to the user type.

In this case, the terminal device for connecting to the wearable device is configured to receive the type signal sent from the wearable device, acquire the user type of the current user according to the type signal, and reduce the default transmission power if the user type of the current user is a user type specified to reduce radiation.

In conclusion, in the method for controlling transmission provided by the present embodiment, the user type of the current user is acquired, and when it is determined that the user type of the current user is the user type specified to reduce radiation, the terminal device is controlled to reduce the default transmission power, thereby solves the problem of strong radiation generated by a terminal device in the prior art, which adopts a default transmission mechanism for optimal signal, and further achieves an effect of reducing radiation for the user types that need to reduce radiation.

Since the terminal device may acquire the user type in various kinds of manners, for example, the terminal device may acquire the defined user type of the current user by means of input manners such as a voice form, a physical keyboard, a virtual keyboard, a touch signal or a shake gesture. For another example, if the terminal device is a mobile phone and a tablet PC that is used by the user in daily life in a contact way, the terminal device may acquire the user type based on the biological parameters of the current user. For another example, if the terminal device is a mobile phone and a tablet PC that is used by the user in daily life in a non-contact way, the terminal device may acquire the user type based on the biological parameters of the current user by means of the wearable device. Two cases in which the user type is acquired based on the biological parameters are respectively described through different embodiments as follows.

Figure 3:
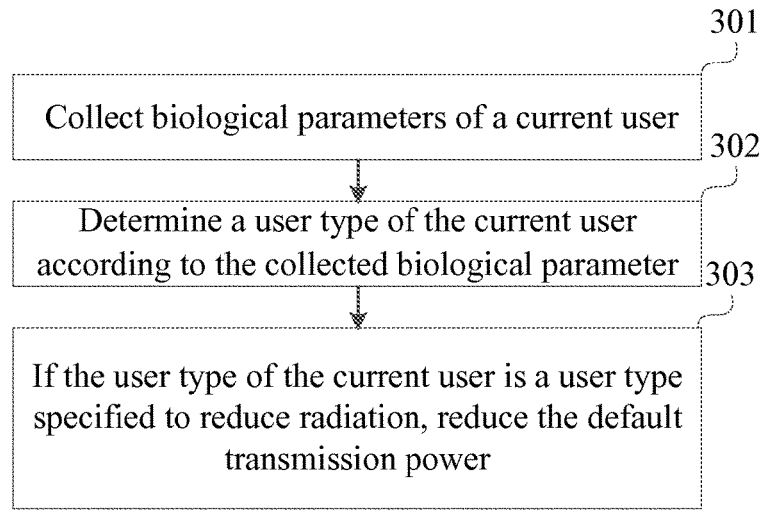
FIG. 3 is a flow diagram illustrating another method for controlling transmission, according to an exemplary embodiment of the present disclosure.

FIG. 3 is a flow diagram illustrating another method for controlling transmission, according to an exemplary embodiment. As shown in FIG. 3, the method for controlling transmission is used in a terminal device, and a user type is acquired by the terminal device based on biological parameters of a current user, the method includes the following steps.

In step S301, the biological parameters of the current user are collected.

The current user wears the wearable device, which can collect biological parameters from the current user. The wearable device may be a smart bracelet or a smart watch or the like. The biological parameters include one ore more parameters of heartbeat, pulse, sleep record, mood record, motion record, temperature record and calorie intake record of a user.

The terminal device acquires the mood record and the calorie intake record of the user by an input from the user. The terminal device monitors and analyses the sleep record, the mood record and the motion record of the user by a tri-axial accelerometer. The terminal device acquires the user's state of mind and pulse by an electrode according to a principle of an electrocardiogram. The terminal device acquires the temperature of the user by a temperature sensor.

In step S302, the user type of the current user is determined according to the biological parameters.

After acquiring the biological parameters of the current user, the terminal device may determine the user type of the current user in a preset corresponding correlation, according to a value of one biological parameter or values of several combined biological parameters. The predetermined corresponding correlation includes a corresponding correlation between different values of the biological parameters and different user types.

That is, after the biological parameters of the current user are collected, the terminal device may determine the user type that matches the value of the biological parameters in the predetermined corresponding correlation, according to the value of the biological parameters.

In step S303, if the user type of the current user is a user type specified to reduce radiation, the terminal device is controlled to reduce the default transmission power.

The user type that needs to have radiation reduced may be the elderly, children or pregnant women. When the user type of the current user is the user type specified to have radiation reduced, the terminal device is controlled to reduce the default transmission power.

If the terminal device is in a communication state (where the terminal device is actively performing communication, such as data communication and voice communication), the terminal device is controlled to determine a transmission power with a condition of satisfying a basic communication quality. To satisfy the basic communication quality, signal intensity may only maintain the basic communication quality rather than an optimal communication quality. On premise that the basic communication quality is maintained, the transmission power is reduced as much as possible. This process may be realized by an empirical threshold. When the signal intensity is lower than the empirical threshold, the transmission power is increased, and when the signal intensity is higher than the empirical threshold, the transmission power is reduced.

If the terminal device is in a standby state, the terminal device is controlled to determine the transmission power with a condition of a minimum radiation value. For example, if a mobile phone is in the standby state, the mobile phone is controlled to determine the transmission power with the condition of the minimum radiation value.

It needs to be further explained that, if the terminal device is in the communication state and the communication is a voice communication, the voice communication is optimized by a predetermined manner, which comprises at least one of audio signal gain amplifying, volume increasing and noise reducing.

In conclusion, in the method for controlling transmission provided by the present embodiment, the user type of the current user is acquired, and when it is determined that the user type of the current user is the user type specified to reduce radiation, the terminal device is controlled to reduce the default transmission power, thereby solves the problem of strong radiation generated by a terminal device in the prior art, which adopts a default transmission mechanism for optimal signal, and further achieves an effect of reducing radiation for the user types that need to reduce radiation.

The transmission power is also determined with the condition of satisfying the basic communication quality when it is in the communication state, such that the effect not only guaranties the normal use of the terminal device but also the radiation may be reduced as much as possible is achieved.

The transmission power is also determined with the condition of the minimum radiation value when it is in the standby state, such that the terminal device keeps the radiation minimum in the standby state.

When the communication is the voice communication, some optimizations other than changing the signal intensity are performed on the voice communication, such that the basic communication quality may be better guarantied.

Figure 4:
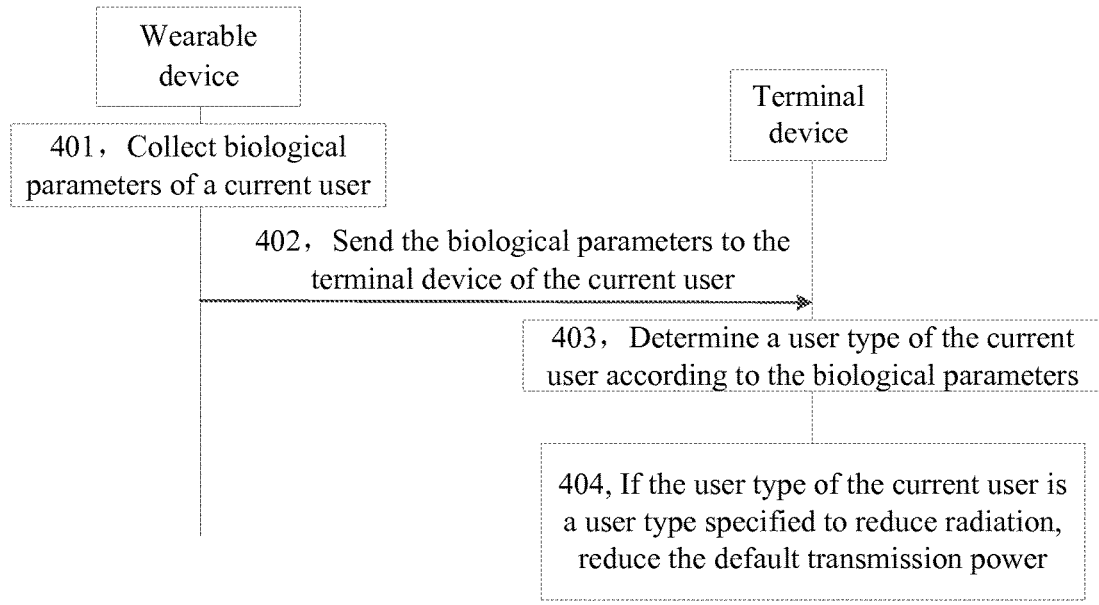
FIG. 4 is a flow diagram illustrating another method for controlling transmission, according to an exemplary embodiment of the present disclosure.

FIG. 4 is a flow diagram illustrating another method for controlling transmission, according to an exemplary embodiment. As shown in FIG. 4, the method for controlling transmission is used in a terminal device and a wearable device, and biological parameters are collected by the wearable device, the terminal device determines a user type based on biological parameters of a current user. Accordingly, the method includes the following steps.

In step S401, the wearable device collects the biological parameters of the current user.

The current user wears the wearable device, which can collect biological parameters from the current user. The wearable device may be a smart bracelet or a smart watch or the like. The biological parameters include one or more parameters of heartbeat, pulse, sleep record, mood record, motion record, temperature record and calorie intake record of a user.

The wearable device may be a smart bracelet or a smart watch or the like. The wearable device acquires the mood record and the calorie intake record of the user by an input from the user. The wearable device monitors and analyses the sleep record, the mood record and the motion record of the user by a tri-axial accelerometer. The wearable device acquires the user's state of mind and pulse by an electrode according to the principle of an electrocardiogram. The wearable device acquires the temperature of the user by a temperature sensor.

In step S402, the wearable device sends the biological parameters to the terminal device of the current user.

The wearable device and the terminal device of the same user are usually connected to each other through a wired or wireless network. For example, a smart bracelet and a smart phone of User A are connected wirelessly through Bluetooth technology or WIFI network.

After collecting the biological parameters of the current user, the wearable device sends the biological parameters to the terminal device of the current user.

Correspondingly, the terminal device receives the biological parameters sent from the wearable device.

In step S403, the terminal device determines the user type of the current user according to the biological parameters.

After acquiring the biological parameters of the current user, the terminal device may determine the user type of the current user in a predetermined corresponding correlation, according to a value of one biological parameter or values of several combined biological parameters. The predetermined corresponding correlation includes a corresponding correlation between different values of the biological parameters and different user types.

That is, after the biological parameters of the current user are received, the terminal device may determine the user type that matches the value of the biological parameters in the predetermined corresponding correlation, according to the value of the biological parameters.

In step S404, if the user type of the current user is a user type specified to reduce radiation, the terminal device is controlled to reduce the default transmission power.

The user type that needs to have radiation reduced may be the elderly, children or pregnant women. When the user type of the current user is the user type specified to reduce radiation, the terminal device is controlled to reduce the default transmission power.

If the terminal device is in a communication state, the terminal device is controlled to determine a transmission power with a condition of satisfying a basic communication quality. To satisfy the basic communication quality, signal intensity may only maintain the basic communication quality rather than an optimal communication quality. On premise that the basic communication quality is maintained, the transmission power is reduced as much as possible. This process may be realized by an empirical threshold. When the signal intensity is lower than the empirical threshold, the transmission power is increased, and when the signal intensity is higher than the empirical threshold, the transmission power is reduced.

If the terminal device is in a standby state, the terminal device is controlled to determine the transmission power with a condition of a minimum radiation value. For example, if a mobile phone is in the standby state, the mobile phone is controlled to determine the transmission power with the condition of the minimum radiation value.

It needs to be further explained that, if the terminal device is in the communication state and the communication is a voice communication, the voice communication is optimized by a predetermined manner, and the predetermined manner includes at least one of audio signal gain amplifying, volume increasing and noise reducing.

In conclusion, in the method for controlling transmission provided by the present embodiment, the user type of the current user is acquired, and when it is determined that the user type of the current user is the user type specified to reduce radiation, the terminal device is controlled to reduce the default transmission power, thereby solves the problem of strong radiation generated by a terminal device in the prior art, which adopts a default transmission mechanism for optimal signal, and further achieves an effect of reducing radiation for the user types that need to reduce radiation.

The transmission power is also determined with the condition of satisfying the basic communication quality when it is in the communication state, such that the effect not only guaranties the normal use of the terminal device but also the radiation may be reduced as much as possible is achieved.

The transmission power is also determined with the condition of the minimum radiation value when it is in the standby state, such that the terminal device keeps the radiation minimum in the standby state.

When the communication state is the voice communication, some optimizations other than changing the signal intensity are performed on the voice communication, such that the basic communication quality may be better guarantied.

The biological parameters of the user are also collected by the wearable device, and inherent characteristics of the wearable device are used, such that hardware conditions and computation amounts required for the terminal device are reduced, resources of the terminal device are saved, and endurance of the terminal device is increased.

Figure 5:
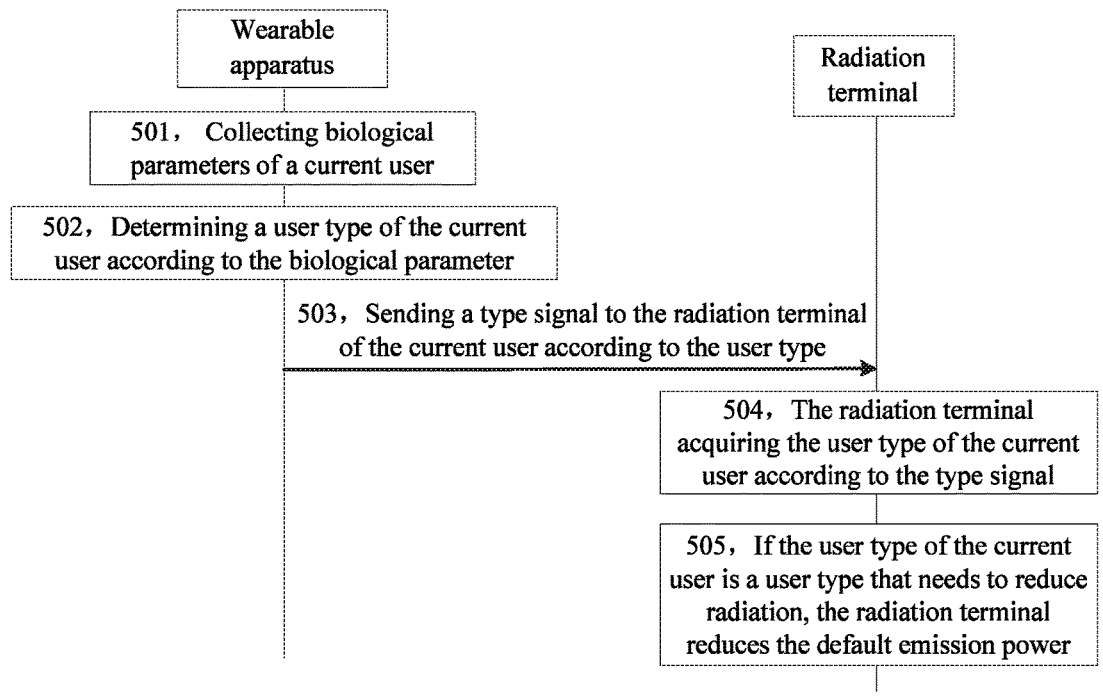
FIG. 5 is a flow diagram illustrating another method for controlling transmission, according to an exemplary embodiment of the present disclosure.

FIG. 5 is a flow diagram illustrating another method for controlling transmission, according to an exemplary embodiment. As shown in FIG. 5, the method for controlling transmission is used in a terminal device and a wearable device, and the wearable device collects biological parameters, and determines a user type based on the biological parameters of a current user, and the method includes the following steps.

In step S501, the wearable device collects the biological parameters of the current user.

The current user wears the wearable device, which can collect biological parameters from the current user. The wearable device may be a smart bracelet or a smart watch or the like. The biological parameters include at one or more parameters of heartbeat, pulse, sleep record, mood record, motion record, temperature record and calorie intake record of a user.

The wearable device may be a smart bracelet or a smart watch or the like. The wearable device acquires the mood record and the calorie intake record of the user by an input from the user. The wearable device monitors and analyses the sleep record, the mood record and the motion record of the user by a tri-axial accelerometer. The wearable device acquires the user's state of mind and pulse by an electrode according to the principle of an electrocardiogram. The wearable device acquires the temperature of the user by a temperature sensor.

In step S502, the wearable device determines the user type of the current user according to the biological parameters.

After collecting the biological parameters of the current user, the wearable device may determine the user type of the current user in a predetermined corresponding correlation, according to a value of one biological parameter or values of several combined biological parameters. The predetermined corresponding correlation includes a corresponding correlation between different values of the biological parameters and different user types.

That is, after collecting the biological parameters of the current user, the wearable device may determine the user type that matches the value of the biological parameters in the predetermined corresponding correlation, according to the value of the biological parameters.

In step S503, the wearable device sends a type signal to the terminal device of the current user according to the user type.

Each user type may respectively correspond to a kind of type signal. The wearable device generates the type signal of the current user according to the user type. Given that the wearable device and the terminal device of the same user are usually connected to each other through a wired or wireless network, the wearable device may send the type signal to the terminal device of the current user through wired or wireless connection.

Correspondingly, the terminal device receives the type signal sent from the wearable device.

It needs to be further explained that, alternatively, in other embodiments, only when the user type of the current user is a user type that needs to reduce radiation, the wearable device may send the type signal to the terminal device, which is not limited by the present embodiment.

In step S504, the terminal device acquires the user type of the current user according to the type signal.

Since each user type may respectively correspond to a kind of type signal, the terminal device may acquire the user type of the current user according to the type signal.

In step S505, if the user type of the current user is the user type specified to reduce radiation, the terminal device reduces a default transmission power.

The user type that needs to have radiation reduced may be the elderly, children or pregnant women. When the user type of the current user is the user type specified to reduce radiation, the terminal device is controlled to reduce the default transmission power.

If the terminal device is in a communication state, the terminal device is controlled to determine a transmission power with a condition of satisfying a basic communication quality. To satisfy the basic communication quality, signal intensity may only maintain the basic communication quality rather than an optimal communication quality. On premise that the basic communication quality is maintained, the transmission power is reduced as much as possible. This process may be realized by an empirical threshold. When the signal intensity is lower than the empirical threshold, the transmission power is increased, and when the signal intensity is higher than the empirical threshold, the transmission power is reduced.

If the terminal device is in a standby state, the terminal device is controlled to determine the transmission power with a condition of a minimum radiation value. For example, if a mobile phone is in the standby state, the mobile phone is controlled to determine the transmission power with the condition of the minimum radiation value.

It needs to be further explained that, if the terminal device is in the communication state and the communication state is a voice communication, the voice communication is optimized by a predetermined manner, and the predetermined manner comprises at least one of audio signal gain amplifying, volume increasing and noise reducing.

In conclusion, in the method for controlling transmission provided by the present embodiment, the user type of the current user is acquired, and when it is determined that the user type of the current user is the user type specified to reduce radiation, the terminal device is controlled to reduce the default transmission power, thereby solves the problem of strong radiation generated by a terminal device in the prior art, which adopts a default transmission mechanism for optimal signal, and further achieves an effect of reducing radiation for the user types that need to reduce radiation.

The transmission power is also determined with the condition of satisfying the basic communication quality when it is in the communication state, such that the effect not only guaranties the normal use of the terminal device but also the radiation may be reduced as much as possible is achieved.

The transmission power is also determined with the condition of the minimum radiation value when it is in the standby state, such that the terminal device keeps the radiation minimum in the standby state.

When the communication is the voice communication, some optimizations other than changing the signal intensity are performed on the voice communication, such that the basic communication quality may be better guarantied.

The wearable device collects the biological parameters of the user, and determines the user type, and inherent characteristics of the wearable device are used, such that hardware conditions and computation amounts required for the terminal device are reduced, resources of the terminal device are saved, and endurance of the terminal device is increased.

Figure 6:
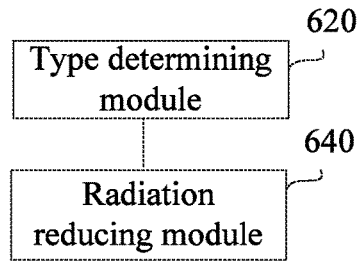
FIG. 6 is a diagram illustrating an apparatus for controlling transmission, according to an exemplary embodiment of the present disclosure.

FIG. 6 is a diagram illustrating an apparatus for controlling transmission, according to an exemplary embodiment. Referring to FIG. 6, the apparatus includes a type determining module 620 and a radiation reducing module 640. For example, the apparatus for controlling transmission as illustrated in FIG. 6 may be configured in the terminal device.

The type determining module 620 is configured to acquire a user type of a current user.

The radiation reducing module 640 is configured to control the terminal device to reduce the default transmission power, when the user type of the current user is a user type specified to reduce radiation.

In conclusion, in the apparatus for controlling transmission provided by the present embodiment, the user type of the current user is acquired, and when it is determined that the user type of the current user is the user type specified to reduce radiation, the terminal device is controlled to reduce the default transmission power, thereby solves the problem of strong radiation generated by a terminal device in the prior art, which adopts a default transmission mechanism for optimal signal, and further achieves an effect of reducing radiation for the user types that need to reduce radiation.

Figure 7A:
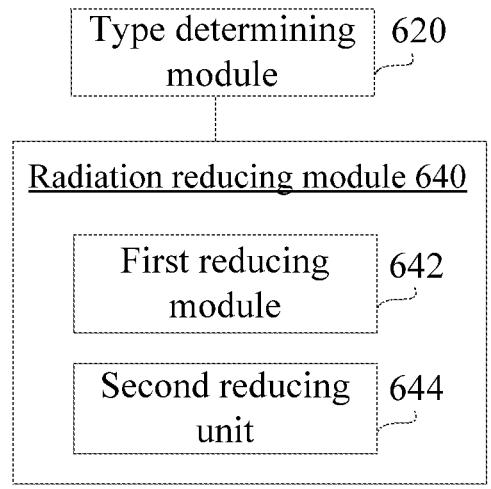
FIG. 7A is a diagram illustrating another apparatus for controlling transmission, according to an exemplary embodiment of the present disclosure.

FIG. 7A is a diagram illustrating another apparatus for controlling transmission, according to an exemplary embodiment. Referring to FIG. 7A, the apparatus may be implemented to be all or a portion of a terminal device by software, hardware or combination thereof. The apparatus includes a type determining module 620 and a radiation reducing module 640.

The type determining module 620 is configured to acquire a user type of a current user.

The radiation reducing module 640 is configured to control the radiation module to reduce the default transmission power, when the user type of the current user is a user type specified to reduce radiation.

Figure 7B:
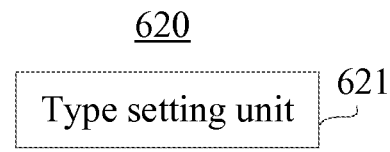
FIGS. 7B-7E are diagrams of four different implementations of a type determining module shown in FIG. 7A.

The type determining module 620 includes a type setting unit 621 configured to receive a defined user type of the current user, as shown in FIG. 7B.

Figure 7C:
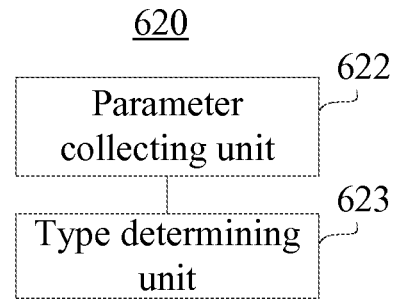

The type determining module 620 further includes a parameter collecting unit 622 configured to collect biological parameters of the current user and a type determining unit 623 configured to determine the user type of the current user according to the biological parameters, as shown in FIG. 7C.

Figure 7D:
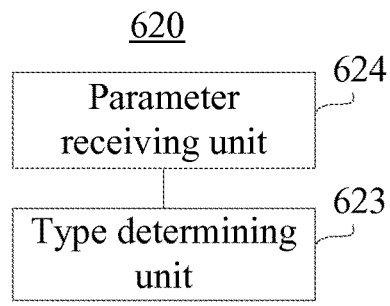

The type determining module 620 further includes a parameter receiving unit 624 configured to receive biological parameters sent from the wearable device, and the biological parameters are sent after the wearable device collects the biological parameters of the current user, and the type determining unit 623 being configured to determine the user type of the current user according to the biological parameters, as shown in FIG. 7D.

Figure 7E:
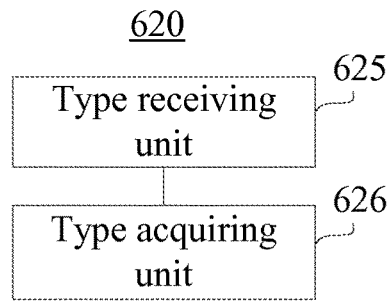

The type determining module 620 further includes a type receiving unit 625 configured to receive a type signal sent from the wearable device and a type acquiring unit 626 configured to acquire the user type of the current user according to the type signal, which is sent after the wearable device collects the biological parameters of the current user and the user type of the current user is determined according to the biological parameters, as shown in FIG. 7E.

The radiation reducing module 640 includes a first reducing unit 642, and/or, a second reducing unit 644.

The first reducing unit 642 is configured to, when the terminal device is in a communication state, control the terminal device to determine the transmission power with the condition of satisfying a basic communication quality.

The second reducing unit 644 is configured to, when the terminal device is in a standby state, control the terminal device to determine the transmission power with the condition of a minimum radiation value.

Alternatively, the apparatus further includes a voice optimizing module 660 configured to, when the terminal device is in the communication state of a voice communication, optimize the voice communication in a predetermined manner, which comprises at least one of audio signal gain amplifying, volume increasing and noise reducing.

In conclusion, in the apparatus for controlling transmission provided by the present embodiment, the user type of the current user is acquired, and when it is determined that the user type of the current user is the user type specified to reduce radiation, the terminal device is controlled to reduce the default transmission power, thereby solves the problem of strong radiation generated by a terminal device in the prior art, which adopts a default transmission mechanism for optimal signal, and further achieves an effect of reducing radiation for the user types that need to reduce radiation.

The transmission power is also determined with the condition of satisfying the basic communication quality when it is in the communication state, such that the effect not only guaranties the normal use of the terminal device but also the radiation may be reduced as much as possible is achieved.

The transmission power is also determined with the condition of the minimum radiation value when it is in the standby state, such that the terminal device keeps the radiation minimum in the standby state.

When the communication is the voice communication, some optimizations other than changing the signal intensity are performed on the voice communication, such that the basic communication quality may be better guarantied.

The wearable device collects the biological parameters of the user, and determines the user type, and inherent characteristics of the wearable device are used, such that hardware conditions and computation amounts required for the terminal device are reduced, resources of the terminal device are saved, and endurance of the terminal device is increased.

Figure 8:
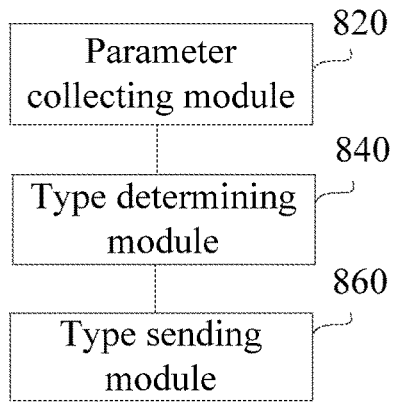
FIG. 8 is a diagram illustrating an apparatus for controlling transmission, according to an exemplary embodiment.

FIG. 8 is a diagram illustrating an apparatus for controlling transmission, according to an exemplary embodiment. Referring to FIG. 8, the apparatus may be implemented to be all or a portion of the wearable device by software, hardware or combination thereof. The apparatus includes a parameter collecting module 820, a type determining module 840 and a type sending module 860.

The parameter collecting module 820 is configured to collect biological parameters of a current user.

The type determining module 840 is configured to determine a user type of the current user according to the collected biological parameters.

The type sending module 860 is configured to send a type signal to a terminal device of the current user according to the user type. In this case, the terminal device connecting with the wearable device is configured to receive a type signal sent from the wearable device, acquire the user type of the current user according to the type signal, and reduce the default transmission power if the user type of the current user is a user type specified to reduce radiation.

With respect to the apparatus in the above embodiments, the specific manners for performing operations for individual modules therein have been described in detail in the embodiments regarding to the methods for controlling transmission, which will not be elaborated herein.

Figure 9:
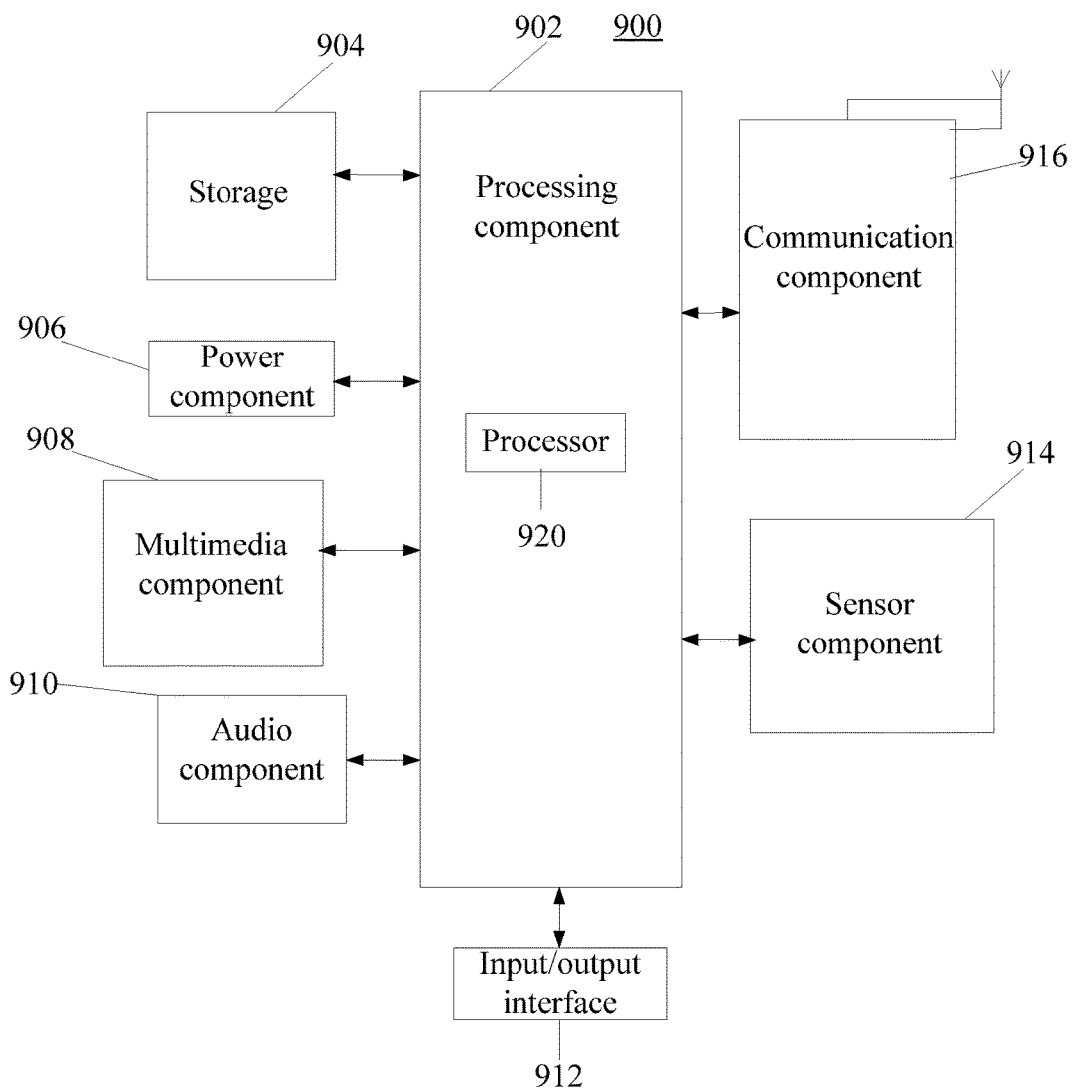
FIG. 9 is a structural block diagram illustrating a terminal device, according to an exemplary embodiment of the present disclosure.

FIG. 9 is a block diagram illustrating a terminal device 900, according to an exemplary embodiment. For example, the terminal device 900 may be a mobile phone, a computer, a digital broadcast terminal, a messaging device, a gaming console, a tablet device, a medical device, exercise equipment, a personal digital assistant, a router and the like.

Referring to FIG. 9, the terminal device 900 may include one or more of the following components: a processing component 902, a storage 904, a power component 906, a multimedia component 908, an audio component 910, an input/output (I/O) interface 912, a sensor component 914, and a communication component 916.

The processing component 902 usually controls the overall operations of the terminal device 900, such as the operations associated with displays, telephone calls, data communications, camera operations, and recording operations. The processing component 902 may include one or more processors 920 to execute instructions to perform all or a part of the steps in the above described methods. Moreover, the processing component 902 may include one or more modules which facilitate the interaction between the processing component 902 and other components. For instance, the processing component 902 may include a multimedia module to facilitate the interaction between multimedia component 908 and the processing component 902.

The storage 904 is configured to store various types of data to support the operations of the terminal device 900. Examples of such data include instructions for any application or method operated on the terminal device 900, contact data, phonebook data, messages, pictures, videos, etc. The storage 904 may be implemented by using any type of volatile or non-volatile memory devices or combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic disk or an optical disk.

The power component 906 provides power to the respective components of the terminal device 900. The power component 906 may include a power management system, one or more power sources, and components associated with the generation, management, and distribution of power for the terminal device 900.

The multimedia component 908 includes a screen providing an output interface between the terminal device 900 and the user. In some embodiments, the screen may include a liquid crystal display (LCD) and a touch panel (TP). If the screen includes the touch panel, the screen may be implemented as a touch screen to receive input signals from the user. The touch panel includes one or more touch sensors to sense touches, swipes, and gestures on the touch panel. The touch sensors may not only sense a boundary of a touch or swipe action, but also sense a duration of time and a pressure associated with the touch or swipe action. In some embodiments, the multimedia component 908 includes a front camera and/or a rear camera. The front camera and/or the rear camera may receive external multimedia data while the terminal device 900 is in an operation mode such as a photographing mode or a video mode. Each of the front camera and the rear camera may be a fixed optical lens system or have focus and optical zoom capability.

The audio component 910 is configured to output and/or input audio signals. For example, the audio component 910 includes a microphone (MIC) configured to receive external audio signals when the terminal device 900 is in an operation mode such as a call mode, a recording mode and a voice recognition mode. The received audio signal may be further stored in the memory 904 or transmitted via the communication component 916. In some embodiments, the audio component 910 further includes a speaker to output audio signals.

The I/O interface 912 provides an interface between the processing component 902 and peripheral interface modules, such as a keyboard, a click wheel, a button, and the like. The button may include, but not limited to, a home page button, a volume button, a starting button, and a locking button.

The sensor component 914 includes one or more sensors to provide status assessments of respective aspects of the terminal device 900. For example, the sensor component 914 may detect an open/closed status of the terminal device 900, relative positioning of components, for example, the display and the keyboard of the terminal device 900, a position change of the terminal device 900 or of a component of the terminal device 900, a presence or absence of a user contacting with the terminal device 900, an orientation or an acceleration/deceleration of the terminal device 900, and a temperature change of the terminal device 900. The sensor component 914 may include a proximity sensor configured to detect the presence of nearby objects without any physical contact. The sensor component 914 may also include a light sensor such as a CMOS or CCD image sensor for use in imaging applications. In some embodiments, the sensor component 914 may also include an accelerometer sensor, a gyroscope sensor, a magnetic sensor, a pressure sensor, or a temperature sensor.

The communication component 916 is configured to facilitate communication, by wire or wirelessly, between the terminal device 900 and other devices. The terminal device 900 may access a wireless network based on a communication standard, such as WiFi, 2G, or 3G, or a combination thereof. In one exemplary embodiment, the communication component 916 receives a broadcast signal or broadcast associated information from an external broadcast management system via a broadcast channel. In one exemplary embodiment, the communication component 916 may further include a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the terminal device 900 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above described methods.

In exemplary embodiments, there is also provided a non-transitory computer readable storage medium including instructions, such as the storage 904 include including the instructions executable by the processor 920 in the terminal device 900, for performing the above-described methods. For example, the non-transitory computer-readable storage medium may be a ROM, a RAM, a CD-ROM, a magnetic tape, a floppy disc, an optical data storage device, and the like.

A non-transitory computer readable storage medium, when instructions in the storage medium are executed by a processor of a terminal device, the terminal device may execute a method for controlling transmission, the method includes acquiring a user type of a current user and controlling the terminal device to reduce a default transmission power if the user type of the current user is a user type specified to reduce radiation.

Respectively, acquiring the user type of the current user comprises receiving a defined user type of the current user.

Alternatively, acquiring the user type of the current user comprises: collecting biological parameters of the current user; and determining the user type of the current user according to the biological parameters.

Alternatively, acquiring the user type of the current user comprises: receiving biological parameters sent from a wearable device; and determining the user type of the current user according to the biological parameters.

Alternatively, acquiring the user type of the current user comprises: receiving a type signal sent from the wearable device; and acquiring the user type of the current user according to the type signal, which is sent after the wearable device collects the biological parameters of the current user and the user type of the current user is determined according to the biological parameters.

Respectively, controlling the terminal device to reduce its default transmission power includes: controlling the terminal device to determine the transmission power with a condition of satisfying a basic communication quality, if the terminal device is in a communication state; and controlling the terminal device to determine the transmission power with a condition of a minimum radiation value, if the terminal device is in a standby state.

Alternatively, controlling the terminal device to reduce the default transmission power includes: optimizing a voice communication, in a predetermined manner, which comprises at least one of audio signal gain amplifying, volume increasing and noise reducing, if the terminal device is in the communication state of the voice communication.

Moreover, the respective components in FIG. 9 may be recombined or deleted to be implemented as a wearable device, and the wearable device may be a smart phone, a smart watch and a smart glasses or the like.

A non-transitory computer readable storage medium, when instructions in the storage medium are executed by a processor of the wearable device, the wearable device may execute a method for controlling transmission, and the method includes: collecting biological parameters of a current user; determining a user type of the current user according to the collected biological parameters; and sending a type signal of the current user to a terminal device according to the user type.

After considering this description and carrying out the embodiments disclosed herein, those skilled in the art may easily anticipate other implementation aspects of the present disclosure. The present disclosure is meant to cover any variations, usage or adaptive change of these embodiments, and these variations, usage or adaptive change follow general concept of the present disclosure and include the common knowledge or the customary technical means in the technical field that is not disclosed in the present disclosure. The description and embodiments are only exemplary, and the real range and concept of the present disclosure are defined by the following claims.

It should be understood that the present disclosure is not limited to precise structures that are described above and shown in the accompanying drawings, and may be modified and changed without departing from the range of the present disclosure. The scope of the present disclosure is only defined by the appended claims.

What is claimed is:

1. A method for controlling transmission in a terminal device, comprising:
    receiving a type signal sent from a wearable device, the type signal obtained, via the wearable device, by collecting biological parameters of a current user and determining that a user type of the current user needs to reduce radiation according to the biological parameters;
    acquiring the user type of the current user according to the type signal;
    reducing, a default transmission power with a condition of satisfying a basic communication quality which guaranties a continuous normal use of the terminal device, if the terminal device is in a voice communication;
    optimizing the voice communication, in a predetermined manner, which comprises at least one of audio signal gain amplifying, volume increasing and noise reducing;
    increasing a transmission power of the terminal device, if the terminal device is in the voice communication state and a signal intensity is lower than an empirical threshold;
    reducing the transmission power of the terminal device, if the terminal device is in the voice communication state and the signal intensity is higher than the empirical threshold;
    wherein the empirical threshold is a signal intensity value at which the terminal device only maintains the basic communication quality in the voice communication;
    wherein the terminal device is any one of a mobile phone, a tablet PC, a router, an e-book reader, a MP3 (Moving Picture Experts Group Audio Layer III) player, a MP4 (Moving Picture Experts Group Audio Layer IV) player, a portable laptop computer and a desktop computer.

2. The method according to claim 1, wherein acquiring the user type of the current user comprises receiving a defined user type of the current user.

3. The method according to claim 1, wherein acquiring the user type of the current user comprises:
    collecting biological parameters of the current user; and
    determining the user type of the current user according to the biological parameters.

4. The method according to claim 1, wherein acquiring the user type of the current user comprises:
    receiving biological parameters sent from a wearable device; and
    determining the user type of the current user according to the biological parameters.

5. A method for controlling transmission in a wearable device, comprising:
    collecting biological parameters of a current user;
    determining that a user type of the current user needs to reduce radiation according to the collected biological parameters;
    sending a type signal of the current user to a terminal device according to the user type; wherein the terminal device is configured to:
    receive the type signal sent from the wearable device;
    acquire the user type of the current user according to the type signal; and
    reduce, a default transmission power with a condition of satisfying a basic communication quality which guaranties the normal use of the terminal device, if the terminal device is in a voice communication; and
    optimize the voice communication, in a predetermined manner, which comprises at least one of audio signal gain amplifying, volume increasing and noise reducing;
    increase a transmission power of the terminal device, if the terminal device is in the voice communication state and a signal intensity is lower than an empirical threshold;
    reduce the transmission power of the terminal device, if the terminal device is in the voice communication state the signal intensity is higher than the empirical threshold;
    wherein the empirical threshold is a signal intensity value at which the terminal device only maintains the basic communication quality in the voice communication;
    wherein the terminal device is any one of a mobile phone, a tablet PC, a router, an e-book reader, a MP3 (Moving Picture Experts Group Audio Layer III) player, a MP4 (Moving Picture Experts Group Audio Layer IV) player, a portable laptop computer and a desktop computer.

6. A terminal device for controlling transmission, comprising:
    a processor; and
    a memory for storing instructions executable by the processor, for performing:
    receiving a type signal sent from a wearable device, the type signal obtained, via the wearable device, by collecting biological parameters of a current user and determining that a user type of the current user needs to reduce radiation according to the biological parameters;
    acquiring the user type of the current user according to the type signal;
    reducing, a default transmission power with a condition of satisfying a basic communication quality which guaranties a continuous normal use of the terminal device, if the terminal device is in a voice communication;
    optimizing the voice communication, in a predetermined manner, which comprises at least one of audio signal gain amplifying, volume increasing and noise reducing;
    increase a transmission power of the terminal device, if the terminal device is in the voice communication state and a signal intensity is lower than an empirical threshold;

reduce the transmission power of the terminal device, if the terminal device is in the voice communication state and the signal intensity is higher than the empirical threshold;

wherein the empirical threshold is a signal intensity value at which the terminal device only maintains the basic communication quality in the voice communication;

wherein the terminal device is any one of a mobile phone, a tablet PC, a router, an e-book reader, a MP3 (Moving Picture Experts Group Audio Layer III) player, a MP4 (Moving Picture Experts Group Audio Layer IV) player, a portable laptop computer and a desktop computer.

7. The terminal device according to claim 6, wherein acquiring the user type of the current user comprises receiving a defined user type of the current user.

8. The terminal device according to claim 6, wherein acquiring the user type of the current user comprises:
collecting biological parameters of the current user; and
determining the user type of the current user according to the biological parameters.

9. The terminal device according to claim 6, wherein acquiring the user type of the current user comprises:
receiving biological parameters sent from a wearable device; and
determining the user type of the current user according to the biological parameters.

10. A wearable device for controlling transmission, comprising:
a processor; and
a memory for storing instructions executable by the processor, for performing:
collecting biological parameters of a current user;
determining that a user type of the current user needs to reduce radiation according to the collected biological parameters;
sending a type signal of the current user to a terminal device according to the user type; wherein the terminal device is configured to:
receive the type signal sent from the wearable device;
acquire the user type of the current user according to the type signal; and
reduce, a default transmission power with a condition of satisfying a basic communication quality which guaranties a continuous normal use of the terminal device, if the terminal device is in a voice communication; and
optimize the voice communication, in a predetermined manner, which comprises at least one of audio signal gain amplifying, volume increasing and noise reducing;
increase a transmission power of the terminal device, if the terminal device is in the voice communication state and a signal intensity is lower than an empirical threshold;
reduce the transmission power of the terminal device, if the terminal device is in the voice communication state and the signal intensity is higher than the empirical threshold;

wherein the empirical threshold is a signal intensity value at which the terminal device only maintains the basic communication quality in the voice communication;

wherein the terminal device is any one of a mobile phone, a tablet PC, a router, an e-book reader, a MP3 (Moving Picture Experts Group Audio Layer III) player, a MP4 (Moving Picture Experts Group Audio Layer IV) player, a portable laptop computer and a desktop computer.

11. A system for controlling transmission, comprising:
a wearable device configured to:
collect biological parameters of a current user;
determine that a user type of the current user needs to reduce radiation according to the collected biological parameters;
send a type signal to a terminal device according to the user type through a wired or wireless network; and
a terminal device configured to:
receive the type signal sent from the wearable device;
reduce, a default transmission power with a condition of satisfying a basic communication quality which guaranties a continuous normal use of the terminal device, if the terminal device is in a voice communication; and
optimize the voice communication, in a predetermined manner, which comprises at least one of audio signal gain amplifying, volume increasing and noise reducing;
increase a transmission power of the terminal device, if the terminal device is in the voice communication state and a signal intensity is lower than an empirical threshold;
reduce the transmission power of the terminal device, if the terminal device is in the voice communication state and the signal intensity is higher than the empirical threshold;

wherein the empirical threshold is a signal intensity value at which the terminal device only maintains the basic communication quality in the voice communication;

wherein the terminal device is any one of a mobile phone, a tablet PC, a router, an e-book reader, a MP3 (Moving Picture Experts Group Audio Layer III) player, a MP4 (Moving Picture Experts Group Audio Layer IV) player, a portable laptop computer and a desktop computer.

12. A system for controlling transmission according to claim 11,
wherein the wearable device is further configured to send the biological parameters of the current user to the terminal device through a wired or wireless network; and
wherein the terminal device is further configured to receive the biological parameters sent from the wearable apparatus, determine the user type of the current user according to the biological parameters, and reduce the default emission power when the user type of the current user is the user type specified to reduce radiation.

* * * * *